US00PP36746P2

(12) United States Plant Patent
Dirr et al.

(10) Patent No.: US PP36,746 P2
(45) Date of Patent: Jun. 17, 2025

(54) ***LOROPETALUM* PLANT NAMED 'LRD-18-20'**

(50) Latin Name: ***Loropetalum chinense* var. rubrum**
Varietal Denomination: LRD-18-20

(71) Applicant: Premier Introductions Inc., Watkinsville, GA (US)

(72) Inventors: Michael Dirr, Bogart, GA (US); Jeff Beasley, Lavonia, GA (US); Mark Griffith, Watkinsville, GA (US)

(73) Assignee: Premier Introductions Inc., Watkinsville, GA (US)

( * ) Notice: Subject to any disclaimer, the term of this patent is extended or adjusted under 35 U.S.C. 154(b) by 0 days.

(21) Appl. No.: 18/762,193

(22) Filed: Jul. 2, 2024

(51) Int. Cl.
*A01H 5/02* (2018.01)
*A01H 6/00* (2018.01)

(52) U.S. Cl.
USPC ..... Plt./226

(58) Field of Classification Search
USPC ..... Plt./226, 263.1
CPC ... A01H 5/02; A01H 5/12; A01H 5/00; A01H 6/00
See application file for complete search history.

(56) References Cited

U.S. PATENT DOCUMENTS

PP18,441 P2 * 1/2008 Berry ..... A01H 6/00 Plt./226
PP25,471 P3 * 4/2015 Kardos ..... A01H 6/00 Plt./226
PP25,534 P3 * 5/2015 Kardos ..... A01H 5/02 Plt./226

* cited by examiner

*Primary Examiner* — June Hwu
(74) *Attorney, Agent, or Firm* — Cassandra Bright

(57) ABSTRACT

A new and distinct cultivar of *Loropetalum chinense* var. *rubrum* plant named 'LRD-18-20', characterized by its compact, mounded, spreading growth habit; dark red foliage color that persists through summer and winter; early blooming pink flowers in spring; and cold hardiness to −13° C.

3 Drawing Sheets

Genus and species of plant claimed: *Loropetalum chinense* var. *rubrum.*

Variety denomination: 'LRD-18-20'.

BACKGROUND OF THE INVENTION

The present invention relates to a new and distinct cultivar of *Loropetalum chinense* var. *rubrum*, a member of the Hamamelidaceae family, hereinafter referred to by its cultivar name 'LRD-18-20'. This cultivar is grown primarily as an ornamental for landscape use and for use as a potted plant.

The cultivar originated from an open-pollination of *Loropetalum chinense* var. *rubrum* 'GriffCRL', U.S. Plant Pat. No. 16,615, in Watkinsville, Georgia, in 2020, and was selected from the progeny by continued evaluation for growth habit, flower, and improved foliage characteristics. The cultivar 'LRD-18-20' originated and was discovered in a cultivated environment in an outdoor nursery in Watkinsville, Georgia.

'LRD-18-20' has been asexually reproduced by softwood cuttings since 2020 in Watkinsville, Georgia. The characteristics of the cultivar have been stable and reproduced true to type in successive vegetative generations.

SUMMARY OF THE INVENTION

'LRD-18-20' has not been observed under all possible environmental conditions. The phenotype may vary somewhat with changes in light, temperature, soil and rainfall without, however, any variance in genotype.

The following traits have been observed and represent the characteristics of the new cultivar. In combination, these characteristics distinguish 'LRD-18-20' from all other varieties in commerce known to the inventor:

1. Compact, mounded, spreading growth habit.
2. Early blooming.
3. Pink flowers in spring.
4. Cold hardy to −13° C.
5. Dark purple foliage.

PARENTAL COMPARISON

Plants of the new cultivar 'LRD-18-20' are comparable to the seed parent in most horticultural characteristics. However, the new variety 'LRD-18-20' differs in the following:

1. 'LRD-18-20' has a compact mounded, spreading growth habit, whereas the seed parent has an overall larger, immense, rounded growth habit.

COMMERCIAL COMPARISONS

Plants of the new cultivar 'LRD-18-20' can be compared to the commercial cultivar 'PIILC-I', U.S. Plant Pat. No. 25,534, in most horticultural characteristics. However, the new variety 'LRD-18-20' differs in the following:

1. 'LRD-18-20' is earlier blooming by about 2 weeks with lighter pink flowers and dark red foliage, whereas 'PIILC-I' has rich reddish-purple foliage that is mounding and bright pink flowers.

Plants of the new cultivar 'LRD-18-20' can be compared to the commercial cultivar 'PIILC-III', U.S. Plant Pat. No.

25,471, in most horticultural characteristics. However, the new variety 'LRD-18-20' differs in the following:

1. 'LRD-18-20' has foliage that is dark red with a pink flower. 'PIILC-III' has foliage that is dark purplish grey and a moderate purplish red flower.

Plants of the new cultivar 'LRD-18-20' can be compared to the commercial cultivar 'LRD-51-22', U.S. Plant Pat. No. 36,424, in most horticultural characteristics. However, the new variety 'LRD-18-20' differs in the following:

1. 'LRD-18-20' is almost twice as tall as 'LRD-51-22'.
2. Foliage of 'LRD-18-20' is almost twice as long (1.7 cm) as foliage of 'LRD-51-22' (1 cm).

BRIEF DESCRIPTION OF THE PHOTOGRAPHS

The accompanying illustrations show characteristics of the new cultivar in photographs as true to color as is reasonably possible to make in illustrations of this nature. Colors in the photographs may differ slightly from the color values cited in the detailed botanical description which accurately describe the colors of the new *Loropetalum*.

DETAILED BOTANICAL DESCRIPTION

Figure 1:
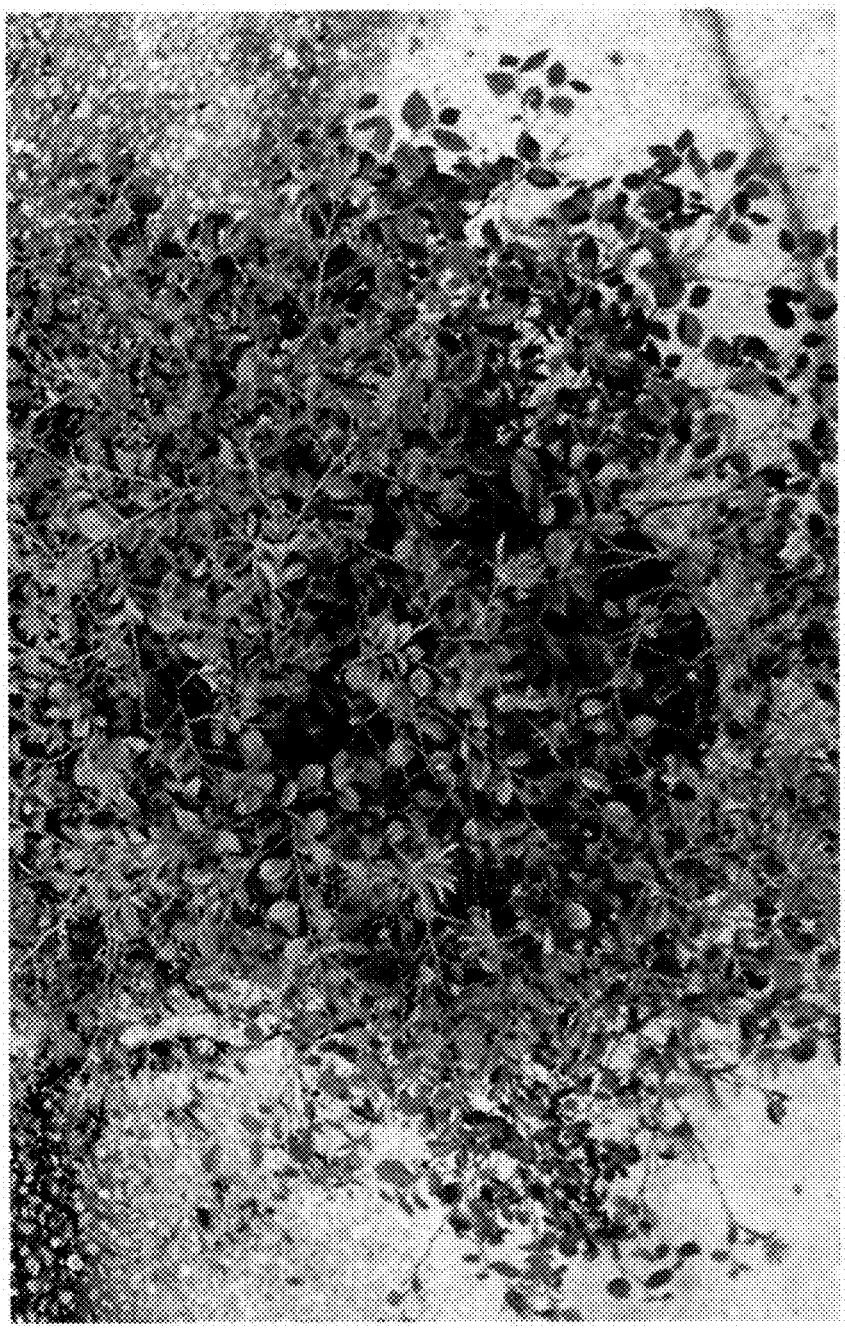
FIG. 1 illustrates the growth habit and flower of a 'LRD-18-20' plant growing in a 5-gallon container. This plant is approximately 3 years old.
Figure 2:
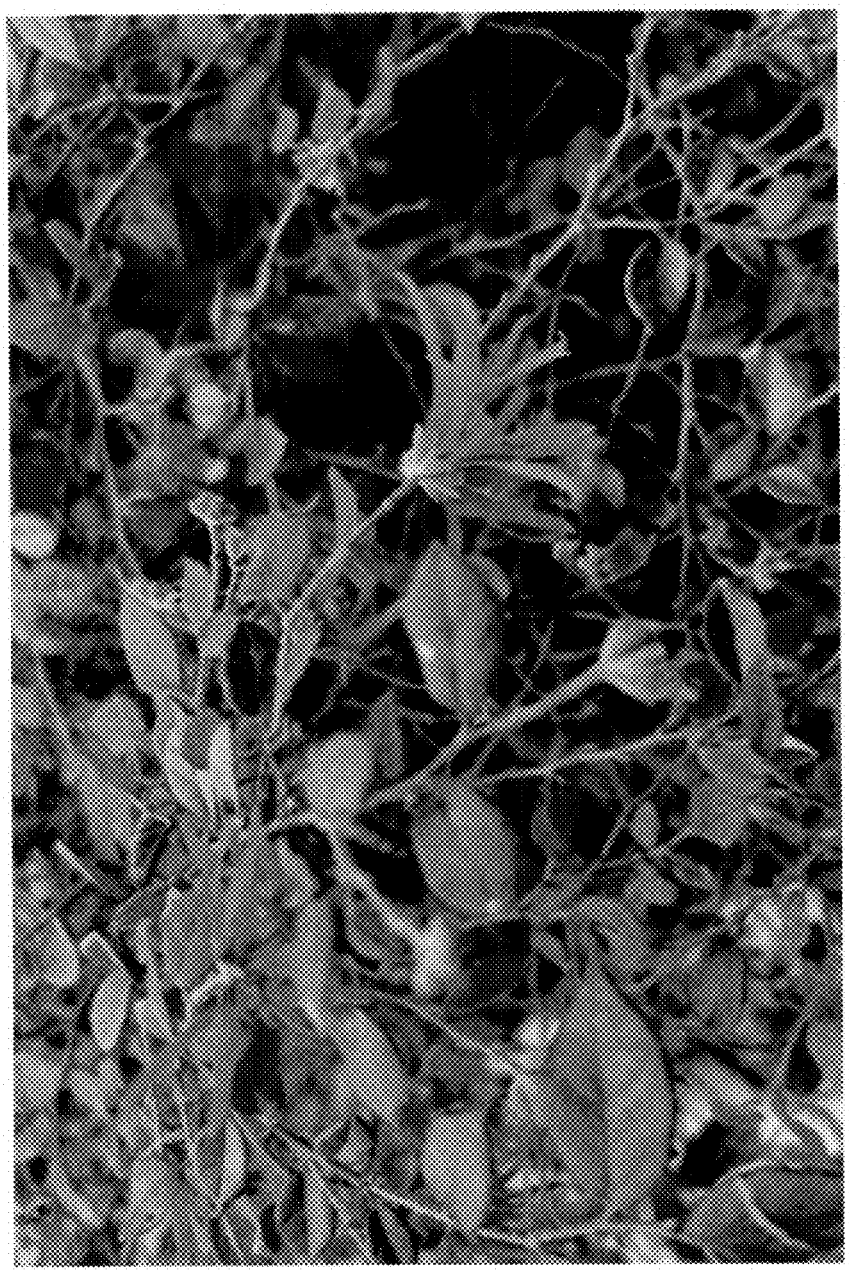
FIG. 2 illustrates a close-up of the flowers of 'LRD-18-20'.
Figure 3:
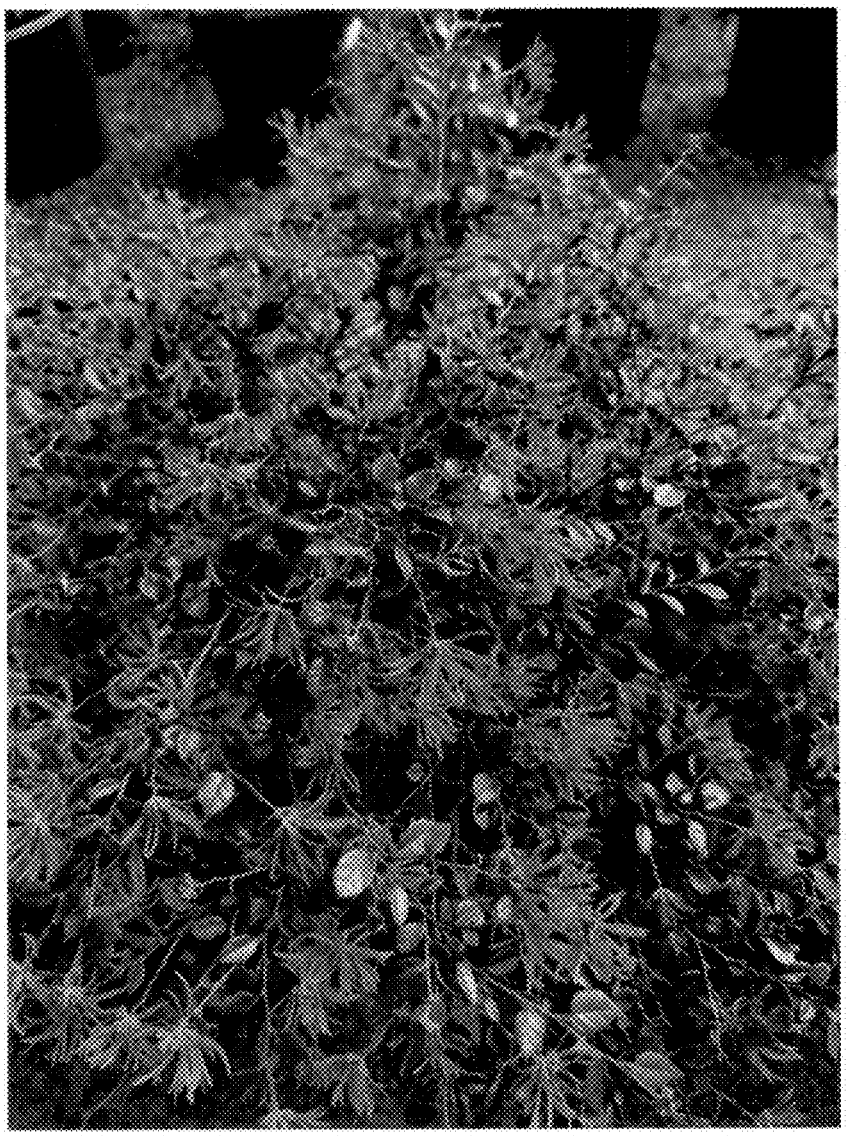
FIG. 3 illustrates growth habit and the foliage and of 'LRD-18-20'.

In the following description, color references are made to The Royal Horticultural Society Colour Chart, 2015 Edition, except where general terms of ordinary dictionary significance are used. Plants for the description were grown in 11.35 liter containers in greenhouse conditions in a nursery in Watkinsville, GA. Plants were about two years old when the description was recorded.

Botanical classification: *Loropetalum chinense* var. *rubrum* 'LRD-18-20'.

PROPAGATION

Type of propagation typically used: Vegetative terminal cuttings.

Time to initiate roots: About 35 days at 32° C. in summer.

Number of days to produce a rooted plant in summer: 110 days at 27° C.

Root description: Numerous, fine, fibrous and well-branched. Colored RHS Greyed-Purple 184A.

PLANT

Type of plant: Flowering shrub.

Age of plant described: 2 years old.

Container size of the plant described: 5-gallon.

Growth habit: Compact, mounded, spreading. Freely branching; pruning enhances lateral branch development.

Height: 21 cm.

Plant spread: 74 cm.

First year stems:

*Length*.—About 17 cm.
*Diameter*.—About 2 mm.
*Shape*.—Round.
*Color*.—RHS Brown 200B.
*Pubescence*.—Heavily stellate.

Second year stems:

*Length*.—20 to 25 cm.
*Diameter*.—3 mm or more.
*Shape*.—Round.
*Color*.—RHS Brown N199B.
*Pubescence*.—None.

Trunk/main stem diameter: About 2 cm at the soil line.

Trunk/main stem color: RHS Brown N199B.

Strength: Flexible when young, more easily broken when mature.

Bark: Exfoliates in flakes beginning on second year stems. Trunk bark flakes are linear, 1-2 cm long and about 1 mm wide. Colored Brown 200C.

Internode length: About 1 cm.

Vegetative buds:

*Arrangement*.—Alternate, imbricate.
*Length*.—About 1 mm.
*Width*.—About 1 mm.
*Color*.—RHS Greyed-Purple 187C.
*Pubescence*.—Stellate.

FOLIAGE

Leaf:

*Arrangement*.—Alternate, simple.
*Average length*.—1.7 cm.
*Average width*.—1 cm.
*Shape of blade*.—Ovate, rounded.
*Apex*.—Pointed.
*Base*.—Oblique.
*Margin*.—Finely-toothed.
*Texture of top surface*.—Scabrous pubescence.
*Texture of bottom surface*.—Scabrous pubescence.
*Color*.—Young foliage upper side: RHS Greyed-Purple 187C. Young foliage under side: RHS Greyed-Purple 187C. Fully expanded foliage upper side: RHS Greyed-Purple 187A. Fully expanded foliage under side: RHS Greyed-Purple 187B. Fall and Winter foliage upper side: RHS Greyed-Purple 187A. Fall and Winter foliage under side: RHS Greyed-Purple 187B. Mature inner leaves upper side: RHS Green NN137A with a hint of Greyed-Purple 187A. Mature inner leaves under side: RHS Green 138A with a hint of Greyed-Purple 187D. Fall and Winter inner leaves upper side: RHS Green NN137A with a hint of Greyed-Purple 187A. Fall and Winter inner leaves under side: RHS Green 138A with a hint of Greyed-Purple 187D.
*Venation*.—Type: Pinnate. Color, young foliage, upper side: RHS Greyed-Purple N187A. Color, young foliage, under side: RHS Greyed-Purple N187A. Color, mature foliage upper side: RHS Greyed-Purple N187A. Color, mature foliage under side: RHS Greyed-Purple N187A.
*Petiole*.—Length: About 3.5 mm. Diameter: About 1 mm. Color: RHS Greyed-Purple 186B. Pubescence: Stellate.

FLOWER

Natural flowering season: Flowers are produced in early April in Watkinsville, GA, and sporadically until frost. An inflorescence is showy for about 2 weeks, and individual flowers last about 2 to 3 days.

Inflorescence and flower type and habit: Umbel produced terminally and from leaf axils.

Inflorescence shape: 4 to 5 strap-like petals forming a loose funnel.
Inflorescence size: 4 cm in height and 8 cm in diameter.
Quantity of florets per inflorescence: 4 to 8.
Persistence: Self-Cleaning.
Fragrance: None.
Flower buds:
*Arrangement.*—4 to 8 flowers from globose heads on branchlet terminals.
*Shape.*—Orbicular.
*Length.*—About 3 mm.
*Diameter.*—About 2 mm.
*Color.*—RHS Red-Purple 59A.
Petals:
*Quantity per flower.*—4.
*Shape.*—Strap-shaped.
*Margin.*—Entire.
*Texture.*—Glabrous.
*Length.*—About 2 cm.
*Width.*—About 2 mm.
*Apex.*—Acuminate.
*Base.*—Obtuse.
*Color.*—Upper surface: RHS Red-Purple N74A. Lower surface: RHS Red-Purple N74A.
Sepals:
*Quantity per flower.*—4.
*Texture.*—Pubescent.
*Arrangement.*—Opposite.
*Shape.*—Ovate.
*Length.*—2 mm.
*Width.*—2 mm.
*Apex.*—Acute to obtuse turning outward.
*Base.*—Fused onto calyx cup.
*Margin.*—Entire.
*Color.*—Upper side: RHS Greyed-Purple 186A. Under side: RHS Greyed-Purple 187C.
Peduncle:
*Length.*—About 8 mm.
*Diameter.*—About 1 mm.
*Texture.*—Stellate.
*Color.*—RHS Greyed-Purple 187A.
Calyx:
*Length.*—About 3 mm.
*Diameter.*—About 2 mm.
*Color.*—RHS Greyed-Purple 187A, both surfaces.
*Pubescence.*—Stellate.

REPRODUCTIVE ORGANS

Stamens:
*Number.*—4 or 5.
*Length.*—1.5 mm.
*Width.*—0.4 mm.
*Color.*—RHS Greyed-Yellow 160B.
*Pollen.*—Amount: Scant. Color: RHS Yellow-Green 157A.
Pistil:
*Number.*—1 or 2 inferior pistils per flower.
*Length.*—Approximately 2 mm.
*Color.*—RHS Red-Purple 71A.
*Style.*—Length: 1 mm. Color: RHS Greyed-Purple 187A.
*Stigma.*—Shape: Rounded. Color: RHS Greyed-Purple 187A. Ovary: Length: 1 mm. Width: 1 mm. Color: RHS Violet 83A.

OTHER CHARACTERISTICS

Temperature tolerance: USDA Plant Hardiness Zone Map (2012): Zone 7 to 9.
Fruits and seeds: Not observed to date.
Disease/pest resistance: Plants of the claimed *Loropetalum* cultivar grown in the garden have not been noted to be susceptible or resistant to pathogens and pests common to Loropetalum.

I claim:

1. A new and distinct *Loropetalum* plant named 'LRD-18-20', substantially as illustrated and described herein.

* * * * *